(12) United States Patent
Olsson

(10) Patent No.: US 6,689,727 B1
(45) Date of Patent: Feb. 10, 2004

(54) AGENT FOR REMOVING ADHESIVE PRODUCTS

(76) Inventor: Bozena Olsson, Håkanstorp 374, SE-246 55 Löddenköpinge (SE)

( * ) Notice: Subject to any disclaimer, the term of this patent is extended or adjusted under 35 U.S.C. 154(b) by 0 days.

(21) Appl. No.: 09/889,679
(22) PCT Filed: Jan. 20, 2000
(86) PCT No.: PCT/SE00/00108
§ 371 (c)(1),
(2), (4) Date: Jul. 19, 2001
(87) PCT Pub. No.: WO00/45776
PCT Pub. Date: Aug. 10, 2000

(30) Foreign Application Priority Data

Jan. 20, 1999 (SE) .................. 9900155

(51) Int. Cl.[7] .............. C11D 7/26; C11D 7/50; C11D 7/52
(52) U.S. Cl. ........ 510/118; 510/119; 510/200; 510/201; 510/203; 510/477; 510/476; 510/488
(58) Field of Search ........... 510/118, 119, 510/130, 138, 158, 159, 200, 201, 203, 477, 476, 488

(56) References Cited

U.S. PATENT DOCUMENTS

| | | | |
|---|---|---|---|
| 3,906,106 A | | 9/1975 | Jacobi ............ 424/312 |
| 5,360,580 A | * | 11/1994 | Dotolo et al. ............ 252/542 |
| 5,891,835 A | * | 4/1999 | Vlasblom ............ 510/143 |
| 5,985,816 A | * | 11/1999 | Vlasblom ............ 510/365 |
| 5,998,352 A | * | 12/1999 | Vlasblom ............ 510/365 |
| 6,096,699 A | * | 8/2000 | Bergemann et al. ........ 510/201 |
| 6,172,031 B1 | * | 1/2001 | Stevens ............ 510/417 |
| 6,225,269 B1 | * | 5/2001 | Baker ............ 510/118 |
| 6,284,720 B1 | * | 9/2001 | Opre ............ 510/170 |
| 6,335,312 B1 | * | 1/2002 | Cofindaffer et al. ........ 510/159 |
| 6,369,016 B1 | * | 4/2002 | Vlasblom ............ 510/365 |

FOREIGN PATENT DOCUMENTS

| | | |
|---|---|---|
| DE | 43 19 913 | 12/1994 |
| EP | 0179675 | 8/1985 |
| EP | 0616016 A1 | 3/1993 |
| EP | 0 755 987 A1 | 1/1997 |
| FR | 2646417 A1 | 11/1990 |
| GB | 884626 | 12/1961 |
| JP | 10036227 A | 2/1998 |
| SE | 503387 | 6/1996 |
| WO | WO 89/07931 | 9/1989 |
| WO | WO 93/15709 | 8/1993 |
| WO | WO 93/18734 | 9/1993 |
| WO | WO 94/16671 | 8/1994 |
| WO | WO9910438 A1 | 3/1999 |
| WO | WO 00/45776 | 8/2000 |

* cited by examiner

Primary Examiner—Gregory Delcotto
(74) Attorney, Agent, or Firm—Boyle Fredrickson Newholm Stein & Gratz, S.C.

(57) ABSTRACT

Composition for removal of nail polish, plaster, adhesives, discolorations or other adhesive products on the skin and/or nails, which to at least 20% includes one or more esters of one or more natural oils, which further includes one or more synthetic esters, and which is substantially free from volatile solvents. The invention also refers to a composition of the same type for paintbrush wash and/or removal of industrial paint or other adhesive products on objects.

28 Claims, No Drawings

AGENT FOR REMOVING ADHESIVE PRODUCTS

CROSS-REFERENCE TO RELATED APPLICATIONS

This case is the United States National Phase filing of PCT application Ser. No. PCT/SE00/00108, filed on Jan. 20, 2000, which claims priority to Sweden Appl. No. 9900155-4; filed Jan. 20, 1999, the entireties of both of which are incorporated by reference herein.

BACKGROUND OF THE INVENTION

1. Field of the Invention

The present invention refers to a composition for the removal of nail polish, adhesive, glue, discolourations or other adhesive products on skin and/or nails, which composition do not contain any volatile solvents. The invention also refers to a composition for removal of colour, varnish or other adhesive products on objects.

2. Description of the Related Art

The most common conventional compositions for removal of nail polish are volatile solvents, such as acetone, or ketone derivatives, with or without the addition of for example oil, the possible oil addition having the purpose to reduce dehydration of the skin and the nails. It also occurs that perfume is added to moderate the smell of solvent.

Due to an increased environmental awareness and thereby increased demands on reduction of the outlet of solvents efforts have been made to replace acetone with other compounds. A closer examination of many of the present nail polish removal compositions on the market today presented as "acetone free" reveals that acetone has been replaced by other solvents which are as harmful as acetone to the environment, often different types of ketones, for example methyl ethyl ketone. Only in Sweden solvents in nail polish removal compositions result in approximately 60 tons of emissions each year.

Other, related problems with conventional solvent based nail polish removal compositions are that they as a consequence of repeated use cause bleached and fragile nails, involve a risk for chronical problems due to inhalation of organic solvents together with that they are inflammable.

One problem encountered during the development of alternative, to the environment more harmless compositions, is that today's nail polishes become more difficult to remove, since they through development have been made better, often with a hardening effect, to prevent undesired wear of the nail polish.

A known nail polish remover, based on conventional solvents such as acetone, is disclosed in GB 884 626. In that patent is also mentioned that the compositions can be designed (prepared) as an emulsion, by the addition of a lipophilic ingredient, for example one or more of different oils or fatty acid esters.

Another known nail polish remover, also based on solvents, is disclosed in DE 43 19 913, wherein it is mentioned that as an additive different types of (synthetic) esters can be used.

From JP 10-36227 (abstract) it is known to use the compounds isopropylmyristate, 2- ethylhexylpalirtate and isobutyloctanoate for removal of water based nail polish, these compounds being inflammable, volatile solvents which furthermore are irritating, allergenic and poisonous to water organisms.

In EP 179 675 there is shown, apart from a number of other compositions, a solvent for nail polish. The composition includes triglycerides ("composition lipidique") which solely constitute a minor part of the composition. The major part of the composition presented in the EP document constitutes inflammable volatile solvents.

U.S. Pat. No. 3,906,106 shows a nail polish remover, which contains 85% of ethyl acetate, which is an inflammable volatile solvent.

In WO 94/16671 and in WO 93/18734 there is shown a composition wherein the disclosed components ethyl lactate and cethyl acetate constitute inflammable volatile or evaporating solvents. Furthermore this composition includes D-limonene, which is a terpene occuring i.a. in natural extracts from oils from e.g. lemon peel. D-limonene has in itself, and in mentioned recipes the characteristics of being inflammable, environmentally hazardous (among other very poisonous for water living microorganisms), not easy degradable, irritating to the health and has furthermore the duty of marking.

JP I-216911 (Abstract) along with WO 89/07931 (Abstract) show a composition for removal of nail polish. The solvents mentioned are volatile or evaporating. Moreover, the compositions are irritating and dehydrating, the reason why the addition of oil is proposed. The oil has however no removing effect in itself.

FR 2,645,417 shows a composition for removal of nail polish which primarily contains acetone, which is an inflammable and volatile solvent.

To sum up, all the above mentioned documents show compositions including inflammable volatile solvents, which result in air pollution and which are dehydrative and possibly allergenic to the skin.

It is further known from SE 504 066 to use one or more lower alkyl esters of fatty acids, for example rape-oil methyl ester, for paintbrush wash and/or removal of paint, such as linseed oil paint, acrylate paint, alkyd oil paint or alkyd/acrylate paint on objects. It is mentioned that the esters should act for 1–2 hours, whereafter the composition is washed off by denaturated alcohol, an aqueous tartaric acid solution or sodium bicarbonate, these washing compositions constituting poisonous/irritating and environmentally hazardous chemical solutions. Thus, it would seem impossible for the skilled person of the present invention to use the composition shown in SE 504066 on humans for removal of nail polish having an essentially different formula or other adhesive products.

As regards the use of the composition shown in SE 504 066 for paintbrush wash or removal of industrial paint on objects, is it also a great disadvantage that the composition needs to act for such a long time, that it has to be removed by the above mentioned washing solutions and that the procedure in certain cases, must be repeated.

It can also be mentioned that the discovery that oil seed rape methyl esters have the effect to solve industrial paint was made in the middle of the 1980's, in connection with the sale of oil seed rape methyl ester (RME) as drive fuel for tractors and agriculture machines. Shortly after, it was discovered that the paint and plastic dissolving effects of RME caused tremendous problems. It was shown that RME had a dissolving effect on paint and contamination coatings on the tank walls, which in turn caused contamination of the fuel. It was further discovered that RME dissolved plastic packages and fuel hoses, which caused fuel leakage.

OBJECTS AND SUMMARY OF THE INVENTION

The primary object of the present invention is to present a composition for the removal of nail polish, plaster, adhesives, discolourations or other adhesive (chemical) products on skin and/or nails, which composition does not include any volatile solvents. Especially, the invention presents a composition for removal of nail polish and/or care of nails, which composition does not include any volatile solvents.

This can be achieved by a composition according to claim 1.

DETAILED DESCRIPTION

The composition is mainly based on natural oils, which preferably are of plant origin and which preferably have a natural nutritional content, including for example different vitamins, the main active substance in the composition being one or more esters, preferably methyl esters, of one or more of these natural oils. The oils are preferably selected from the group consisting of oil seed rape oil, almond oil, sunflower oil, olive oil, maize oil, coconut oil, lemon oil and mixtures of oils. A mixture of oils here means a mixture of natural oils, mainly of plant origin, e.g. conventional so-called food oil. Most preferred is a methyl ester of oil seed rape oil, so-called oil seed rape methyl ester, to which esters of more exclusive oils can be added to increase the exclusiveness of the composition and/or to add vitamins etc. Very exclusive compositions can be based substantially on esters of the superior oils, such as almond oil, coconut oil or lemon oil.

The fatty acid part of the ester/esters of natural oils can be one or more aliphatic ($C_8$–$C_{22}$) monocarboxylic acids, preferably ($C_{12}$–$C_{22}$) monocarboxylic acids. As an example of a possible composition of oil seed rape methyl ester the following is mentioned:

| Ester | Amount % by weight |
| --- | --- |
| $C_{11}H_{23}COOCH_3$ | 0–1 |
| $C_{13}H_{27}COOCH_3$ | 0–1 |
| $C_{15}H_{31}COOCH_3$ | 2–8 |
| $C_{17}H_{35}COOCH_3$ | 0–6 |
| $C_{17}H_{33}COOCH_3$ | 50–60 |
| $C_{17}H_{31}COOCH_3$ | 18–27 |
| $C_{17}H_{29}COOCH_3$ | 6–12 |
| $C_{19}H_{39}COOCH_3$ | 0–2 |

The composition may exclusively consist of such ester/esters of natural oils, i.e. up to 100%. However, according to the invention the composition comprises additives of one or more synthetic, organic esters, suitably in an amount of 20–80%, preferably 30–60%, even more preferably 35–60%, this/these suitably comprising: dimethylsuccinate in an amount of 5–30%, preferably 5–25% and even more preferably 16–20% and/or dimethylglutarate in an amount of 20–70%, preferably 25–60% and even more preferably 35–50% and/or dimethyladipate in an amount of 3–30%, preferably 3–25% and even more preferably 15–20%.

Instead of separate additions of dimethylsuccinate, dimethylglutarate and dimethyladipate as above, a ready-made composition can be added in an amount of 20–80%, preferably 30–60% and even more preferably 35–60% of the composition. Such a ready-made composition is produced by Du Pont and marketed in Sweden by Chematex under the trademark Dibasisk ester (Dibasic ester, article number 1063), also named DBE. The amount of the three esters can vary in DBE from different producers, but is normally in the intervals 12–30% dimethylsuccinate, 50–70% dimethylglutarate and 8–30% dimethyladipate.

To give the composition an increased removing effect N-methyl-2-pyrrolidone can also be added in an amount of 0–5%, preferably 0–2% or 0.1–5%, preferably 0.2–2%. Alternatively to N-methyl-2-pyrrolidone or in combination therewith, dimethylsulfoxide can be added in an amount of 0–10%, preferably 0–5% and even more preferably 0–2% or 0.1–10%, preferably 0.2–5% and even more preferably 0.2–2%. It has during the development of the invention been found that the addition of N-methyl-2-pyrrolidone or dimethylsulfoxide is especially advantageous when nail polish should be removed from synthetic nails, but also that it has an effect when removing nail polish from natural nails. An especially advantageous effect is obtained with modern, hardened nail polish. Even alternative auxiliary chemicals in small amounts, within the above mentioned ranges, can be used in the composition. In a composition according to the invention, which is specifically adapted to allergic persons the use of N-methyl-2-pyrrolidone should be minimised or completely avoided.

The content of esters of natural oils in the composition is at least 20%, preferably at least 35% and even more preferably at least 50%, preferably not more than 80% and even more preferably not more than 70%. The content of esters of natural oils is suitably 20–80%, preferably 35–70% and even more preferably 50–70%.

The composition may also include vitamins, which is specifically preferred when the natural oils on which the composition is based is poor in vitamins. Vitamins added can include vitamin A, vitamin B, vitamin D and vitamin E. Vitamins can also be added in the form of natural oils which are naturally high in nutritional content, e.g. pure oil seed rape oil or another oil, preferably in amounts of 0.1–5%. Such an addition of oil can give an extra caring effect on skin/nails.

The composition is preferably non-perfumed and not tested on animals.

Conventional nail polish, which primarily is intended to be removed by means of the composition according to the invention, include volatile solvents such as ketones, for example acetone, methyl ethyl ketone and the like, acetic acid butyl esters, for example butyl acetate, ethyl acetate and the like. The composition according to the invention is also active on nail polish based on similar types of volatile solvents.

Conventionally nail polish includes compounds from the group consisting of butyl acetate (an aliphatic ester), ethyl acetate (an aliphatic ester), acetone, methyl ketone, nitrocellulose, toluene (minimal amounts), dibutyl ftalate, camfora, Steralkonium Hectorite. The development within the area has been towards more and more hazardous solvents, to obtain stronger nail polish.

In use the composition is applied to the nails, the composition advantageously being provided in disposable napkins impregnated with the composition, which disposable napkins are individually packed in cover wrapped packages or packed in resealable multipack. It has proved to be specifically advantageous to use disposable napkins based on fibres, especially of cotton, since cotton has a natural capacity to absorb the dissolved nail polish. After a few seconds the nail polish may be wiped off. After the treatment the nails may, if desired, be painted again with nail polish, without any further type of cleansing. The consumed disposable napkin is compostable and degradable to more than 90%.

The composition has also proved to be active in removing other types of unwanted, adhesive (chemical) products which one more or less unintentionally may get on the skin and/or the nails. Such products can e.g. be remainders of adhesives, jointing material, cement, binding agent, hardener, putty and other organic compounds, industrial paints or varnishes, remainders of plaster or discolourations on the skin/nails, which are difficult to remove by common soap and water.

A composition according to the invention for removal of plaster, adhesives, discolourations or other adhesive products on skin/nails is very suitable to be used in nursing or in workshops, construction sites or other similar working places. As regards the plaster removing effect the composition has a great advantage in that it is not irritating to the skin, since many people do get skin problems in connection with the use of or the removal of plasters.

The composition may possibly, when intended to be used on the skin, be mixed with an abrasive, e.g. in the form of pumice or plastic pellets, to increase the removing effect. Possibly, the composition may be formed as a paste.

Since the composition is based on natural products, the colour may vary without the effect of the product being affected.

The main advantages of the composition are the fact that it is not irritating, is environmentally adapted, is not based on volatile solvents, does not evaporate and is not inflammable. According to existing regulations it is not necessary to mark such products.

It has also surprisingly been found during the development of the invention, that the composition has a treating/caring effect on the nails and the cuticles, whereby these after repeated treatments become strong and healthy. The reason for this seems to be the softening, lipid character of the esters and its natural content of vitamins and trace elements etc. Thus the composition has a double effect: nail polish removing as well as curing, whereby the user will save time and money in avoiding to spend separate time on curing the nails.

EXAMPLE 1

As an example of a composition according to the invention for removal of nail polish or other adhesive chemicals on skin and/or nails, the following preferred formula is given:

| Oil seed rape methyl ester | 55% |
|---|---|
| Dibasic ester | 44–44.5% |
| N-methyl-2-pyrrolidone | 0.5–1% |

N-methyl-2-pyrrolidone can also be replace with another suitable chemical additive or be completely excluded.

It has further been found during the development of the invention that the composition also may be utilised for removing other types of varnishes or paints used within the industrial area, in any case varnishes and paints on metals or metal alloys. According to one aspect the varnish or the paint, which is intended to be removed, may include a hardener. It may be especially interesting to use the composition for removal of varnish/paint on metal sheet, e.g. car metal sheet, thus renovation of veteran cars etc. being an applicable area. In this type of industrial application it may be appropriate to add N-methyl-2-pyrrolidone and/or dimethylsulphoxide and/or another effect improving chemical additive in an increased amount, however preferably below 50%, e.g. 0–30% or 0–20% of each or one of the two, preferably at a minimum of 1% and under 50%, more preferably 5–30% or 5–20%.

The invention also concerns a composition for paintbrush wash and/or removal of industrial paint or other adhesive (chemical) products on objects, according to the claims.

Examples of industrial paints, which may be removed are paints within the group consisting of alkyd or alkyd oil paint, powder varnishes, emulsion paints, acetone varnishes/paints or varnishes/paints based on other ketones, rust preventive paints, limewash, glue paint, alkyl paints, acrylate paints, alkyd/acrylate paints, linseed oil paint, asphalt paints, plastic paints. Alkyd or alkyd oil paints, those based only on white spirit as well as those including additions of other natural oils, e.g. linseed oil, pine oil, soy been oil, fish oil or Chinese wood oil, may be removed by the composition according to the invention.

Examples of other adhesive products on objects, which may be removed by the composition according to the invention are products from the group consisting of glue, plastics, binding agents, putty, jointing material, asphalt, cement or other filling material. In this connection the composition may also be used to wash e.g. tools to be used in connection with the above mentioned products.

EXAMPLE 2

As an example of a composition according to the invention for the wash of paintbrushes and/or removal of industrial paint or other adhesive products the following preferred composition is presented:

| Oil seed rape methyl ester | 51% |
|---|---|
| Dibasic ester | 35% |
| N-methyl-2-pyrrolidone | 14% |

The composition according to the invention for paintbrush wash or removal of industrial paint on objects present, as compared to SE 504066, the advantages that the composition due to the additives to the ester/esters of the natural oils, acts very fast in one treatment step only, after which the dissolved paint may be easily wiped off with a cloth (preferably a cotton cloth). The composition according to the invention is also active on other types of varnishes or paint than those specified in SE 504 066.

The invention is not restricted to the above mentioned embodiments, but may be varied within the scope of the patent claims. All the %-ranges mentioned are intended to mean % by weight.

What is claimed is:

1. A composition for the removal of nail polish, plaster, adhesives, discolourations or other adhesive products on skin and/or nails comprising:
    a) 20–80% of one or more esters of one or more natural oils,
    b) 20–80% of one or more of dimethylsuccinate, dimethylglutarate or dimethyladipate, wherein the composition is substantially free from volatile solvents.

2. The composition according to claim 1, wherein the composition contains 20–80% (w/w) of a), 20–80% (w/w) of b) and 0.1–5% of N-methyl-2-pyrrolidone and/or 0.1–10% of dimethylsulfoxide.

3. The composition according to claim 2, wherein the composition contains 35–70% (w/w) of a), 30–60% (w/w) of b) and 0.2–2% of N-methyl-2-pyrrolidone and/or 0.2–5% of dimethylsulfoxide.

4. The composition according to claim 3, wherein the composition contains 50–70% (w/w) of a), 35–60% (w/w) of b) and 0.2–2% of N-methyl-2-pyrrolidone and/or dimethylsulfoxide.

5. A composition for the removal of nail polish, plaster, adhesives, discolourations or other adhesive products on skin and/or nails comprising:
   a) 20–80% of one or more esters of one or more natural oils,
   b) 20–80% of one or more of dimethylsuccinate, dimethylglutarate or dimethyladipate, wherein the composition is free from volatile solvents and wherein the composition further includes one or more vitamins selected from the group consisting of vitamin A, vitamin B, vitamin D and vitamin E.

6. The composition according to claim 1, wherein the adhesive product is a product selected from the group consisting of nail polish, adhesives, plaster, jointing agents, cement, binding agents, hardener, putty or other organic preparations, industrial paints or varnishes, parts of plasters and discolourations.

7. The composition according to claim 1, wherein the composition is absorbed in disposable napkins.

8. The composition according to claim 1, wherein the composition is absorbed in disposable fibre based napkins.

9. The composition according to claim 8, wherein the composition is absorbed in disposable cotton napkins.

10. A composition for paintbrush wash and/or removal of industrial paint or other adhesive products on objects consisting of;
    a) 20–80% of one or more esters of one ore more natural oils,
    b) 20–80% of one or more of dimethylsuccinate, dimethylglutarate or dimethyladipate.

11. The composition according to claim 10, wherein the composition contains 20–80% (w/w) of a), 20–80% (w/w) of b) and less than 50% of N-methyl-2-pyrrolidone and/or dimethylsulfoxide.

12. The composition according to claim 11, wherein the composition contains 35–70% (w/w) of a), 30–60% (w/w) of b) and 5–30% of N-methyl-2-pyrrolidone and/or dimethylsulfoxide.

13. The composition according to claim 12, wherein the composition contains 50–70% (w/w) of a), 35–60% (w/w) of b) and 5–20% of N-methyl-2-pyrrolidone and/or dimethylsulfoxide.

14. The composition according to claim 10, wherein the adhesive product is a product selected from the group consisting of alkyd or alkyd oil paints, powder varnishes, emulsion paints, acetone varnishes/paints or varnishes/paints based on ketones, rust preventive agents, limewash, glue paint, alkyl paints, acrylate paints, alkyd/acrylate paint, linseed oil paint, asphalt paint and plastic paint.

15. The composition according to claim 10, wherein the adhesive product is a product selected from the group consisting of adhesives, plastics, binding agents, putty, jointing material, asphalt, cement or other filling material.

16. The composition according to claim 10, wherein the composition is absorbed in disposable napkins.

17. The composition according to claim 16, wherein the composition is absorbed in disposable fibre basked napkins.

18. The composition according to claim 16, wherein the composition is absorbed in disposable cotton napkins.

19. The composition of claim 1, further comprising: N-methyl-2-pyrrolidone and/or dimethylsulfoxide.

20. The composition of claim 10, further comprising: N-methyl-2-pyrrolidone and/or dimethylsulfoxide.

21. A composition for the removal of nail polish, plaster, adhesives, discolourations or other adhesive products on skin and/or nails comprising:
    a) one or more esters of one or more natural oils,
    b) one or more synthetic organic esters selected from the group consisting of dimethylsuccinate, dimethylglutarate and dimethyladipate,
    wherein the ratio of the one or more esters of the one or more natural oils to the one or more synthetic organic esters provides effective amounts thereof to remove nail polish, plaster, adhesives, discolourations or other adhesive products on human skin, a human nail, or a nail attached to a human nail, and
    wherein the composition is free of volatile solvents.

22. The composition according to claim 21, wherein the composition comprises:
    a) 20–80% of one or more esters of one or more natural oils,
    b) 20–80% of one or more of dimethylsuccinate, dimethylglutarate or dimethyladipate.

23. A composition for the removal of nail polish, plaster, adhesives, discolourations or other adhesive products on skin and/or nails comprising:
    a) one or more methyl esters of one or more natural oils,
    b) one or more synthetic organic esters selected from the group consisting of dimethylsuccinate, dimethylglutarate and dimethyladipate,
    wherein the composition comprises one of a vitamin A, vitamin B, vitamin D, and vitamin E,
    wherein the ratio of the one or more methyl esters of the one or more natural oils to the one or more synthetic organic esters provides effective amounts thereof to remove nail polish, plaster, adhesives, discolourations or other adhesive products on skin or nails, and
    wherein the composition is free of volatile solvents.

24. The composition according to claim 23, wherein the composition comprises:
    a) 20–80% of one or more methyl esters of one or more natural oils,
    b) 20–80% of one or more of dimethylsuccinate, dimethylglutarate or dimethyladipate, and
    wherein the 20–80% of one or more methyl esters of one or more natural oils comprises a naturally high nutritional content oil in an amount of 0.1–5% that provides one vitamin selected from the group consisting of vitamin A, vitamin B, vitamin D, and vitamin E.

25. A composition for the removal of nail polish or an adhesive on skin and/or nails comprising:
    a) an ester from a natural oil selected from one of the following natural oils: oils seed rape oil, almond oil, sunflower oil, olive oil, maize oil, coconut oil, lemon oil, and combinations thereof,
    b) a synthetic ester selected from one of the following: dimethylsuccinate, dimethylglutarate, dimethyladipate, and combinations thereof,
    wherein the ratio of the natural oil ester to the synthetic ester provides effective amounts thereof to remove nail polish or an adhesive on skin or nails, and
    wherein the composition is free from volatile solvents.

26. The composition according to claim 25, wherein the synthetic ester comprises between 12–30% dimethylsuccinate, between 50–70% dimethylglutarate, and between 8–30% dimethyladipate.

27. A composition for the removal of nail polish or an adhesive on skin and/or nails consisting of:
   a) one or more esters from one or more natural oils selected from one of the following natural oils: oil seed rape oil, almond oil, sunflower oil, olive oil, maize oil, coconut oil, and lemon oil, and
   b) one or more synthetic esters selected from one or more of the following constituents: dimethylsuccinate, dimethylglutarate, and dimethyladipate, and
   wherein the composition is free from volatile solvents.

28. A composition for the removal of nail polish or an adhesive consisting of:
   a) a plurality of synthetic organic esters in an amount between 35% and 60% by weight including at least one of dimethylsuccinate, in an amount between 16% and 20% by weight, dimethylglutarate, in an amount between 35% and 50% by weight, and dimethyladipate, in an amount between 15% and 20% by weight,
   b) at least one natural oil ester of aliphatic composition in an amount of at least 20% by weight and not more than 80% by weight, with the at least one natural oil ester selected from the group of oil seed rape oil, almond oil, sunflower oil, olive oil, corn oil, coconut oil, lemon oil, or a mixture thereof,
   c) one of N-methyl-2-pyrrolidone, in an amount of at least 0.2% and less than 50% by weight, and dimethylsulfoxide, in an amount of at least 0.2% and less than 50% by weight.

* * * * *